United States Patent
Intelisano

(12) 
(10) Patent No.: US 6,440,448 B1
(45) Date of Patent: Aug. 27, 2002

(54) FOOD SUPPLEMENT/HERBAL COMPOSITION FOR HEALTH ENHANCEMENT

(76) Inventor: Joseph Intelisano, P.O. Box 251- The Hideout, Lake Ariel, PA (US) 18436-0251

( * ) Notice: Subject to any disclaimer, the term of this patent is extended or adjusted under 35 U.S.C. 154(b) by 0 days.

(21) Appl. No.: 09/039,427

(22) Filed: Mar. 16, 1998

(51) Int. Cl.$^7$ .................. A61K 47/00; A61K 35/78; A01N 65/00
(52) U.S. Cl. .................................. 424/439
(58) Field of Search .................. 424/439, 195.1; 800/DIG. 23

(56) References Cited

U.S. PATENT DOCUMENTS

| | | | |
|---|---|---|---|
| 4,258,037 A | 3/1981 | Juvin | 424/195 |
| 4,339,435 A | 7/1982 | Adachi et al. | 424/195 |
| 4,474,771 A | 10/1984 | Morita | 424/195 |
| 4,496,539 A | 1/1985 | Plotkin et al. | 424/94 |
| 4,618,495 A | 10/1986 | Okuda et al. | 424/195.1 |
| 4,645,667 A | 2/1987 | Hashimoto et al. | 424/92 |
| 4,678,773 A | 7/1987 | Usami et al. | 514/25 |
| 4,704,279 A | 11/1987 | Hancock | 424/195.1 |
| 4,786,496 A | 11/1988 | Watanabe et al. | 424/195.1 |
| 4,822,612 A | 4/1989 | Shinpo | |
| 4,952,399 A | 8/1990 | Lewenstein et al. | 424/195.1 |
| 4,976,960 A | 12/1990 | Grossman et al. | 424/195.1 |
| 5,002,766 A * | 3/1991 | Ransherger | 424/94.2 |
| 5,053,386 A | 10/1991 | Tung | 514/2 |
| 5,064,675 A | 11/1991 | Jensen et al. | 426/597 |
| 5,141,958 A | 8/1992 | Crozier-Willi et al. | 514/558 |
| 5,248,503 A * | 9/1993 | Emanuel-King | 424/195.1 |
| 5,330,759 A | 7/1994 | Pagay et al. | 424/462 |
| 5,338,547 A | 8/1994 | Kennedy et al. | 424/195.1 |
| 5,405,613 A * | 4/1995 | Rowland | 514/195.1 |
| 5,437,866 A * | 8/1995 | Sun | 424/195.1 |
| 5,482,711 A | 1/1996 | Medenica | 424/195.1 |
| 5,484,594 A | 1/1996 | Frangi et al. | 424/195.1 |
| 5,632,983 A * | 5/1997 | Hadden | 424/85.1 |
| 5,744,187 A * | 4/1998 | Gaynor | 426/599 |

FOREIGN PATENT DOCUMENTS

RU  2008013  * 2/1994

OTHER PUBLICATIONS

The Merck Manual 16th ed. Merck & Co., Inc. Rahway, N.J. p. 646 Asthma, 1992.*
Medical Essay, Supplement to Mayo Clinic Health Letter, pp. 1–8, Jun. 1997.*
Wiley and Sons, Hydrogen peroxide induced modulation of intracellular oxidized states in cultured macrophage J774A.1 and neuroactive PC12–cells, and protection by a novel grape seed proanthocyanidin extract, AN 1999:93946 CAPLUS, 1998.*
Pouvreau et al, Effect of pea and bovine trypsin inhibitors on wild–type and miodified trypsins, AN1998:121276, CAPLUS, 1998.*
"Menu Analysis", 1981, Joseph Intelisano, B.S., D.C.
"Menu Analysis for Serious Lung & Urogenital Conditions", 1981, Joseph Intelisano, B.S., D.C.

* cited by examiner

*Primary Examiner*—Avis M. Davenport
(74) *Attorney, Agent, or Firm*—Stevens, Davis, Miller & Mosher, L.L.P.

(57) ABSTRACT

A composition and method of using extracts to form a compound or compounds of what are termed food supplements, which comprise in combination (i) essential antioxidant ingredients and materials characterized by their stability for an extended period of time while in the dry state and under ambient conditions; (ii) said antioxidant ingredients and materials are selected from a group consisting of extracts of animal tissue and/or plant tissue; (iii) in an orally ingestible carrier such as capsules, tablets, a dried form as in a tea, a diluent, or any other delivery system, for (iv) the treatment of animals, including humans, to ameliorate the effects of lung conditions or other degenerative conditions due to aging.

12 Claims, No Drawings

FOOD SUPPLEMENT/HERBAL COMPOSITION FOR HEALTH ENHANCEMENT

BACKGROUND OF THE INVENTION

As is well known there are many vitamins and minerals, essential fatty acids, proteins and carbohydrates which are required to sustain the human body. Recently the lack of vitamins, minerals and essential-unsaturated fatty acids have been linked to the creation of various diseases, more specifically those diseases of aging such as in arthritis and cancer as well as others. Recently noted is the evidence that the unsaturated fatty acids and their derivatives, e.g.: salts, amides, and esters, play a role in the synthesis of prostaglandin which are local hormones which have multiple physiological functions.

SUMMARY OF THE INVENTION

In addition to the above, a great number of naturally occurring ingredients in substances not normally taken into the diet are known to inhibit or reduce the growth of tumor cells. Some examples of these rarely ingested items are what are termed herbs, edible fungus, e.g. mushrooms and antioxidants from natural raw sources such as grape seed or the Merritime pine bark. Although most, if not all, of the ingredients to be listed under this invention have a mildly positive effect in nourishing all cells, it is the intent of this invention to stimulate the positive effects of aiding in the body's natural defensive mechanisms and, therefore, through increasing natural immunity, aid in inhibiting the growth of malignant cells.

The present invention therefore extracts data from several well known areas of established Alternative healing. These areas include but are not limited to the following: Ayurvedic Medicine, Chinese Herbology/Medicine, American and/or English Herbology, Homeopathic Medicine, and the known methods in the art of cold pressed glandular extractions. Also included are the areas known as antioxidant and nutritional therapy. The various herbs, mushrooms and other extracts are known in the art to have a positive effect upon inhibiting the growth and metastases of malignant cells, removal of the mucous debris from malignant cellular death and a general cleansing action of the body's toxicity via the blood and lymphatic systems.

The antioxidants listed in this invention are known to play a role in inhibiting degenerative processes. Amongst the degenerative conditions discussed in the body of common knowledge of the art, the following are considered degenerative diseases, but by no means is the list limited to these conditions. Examples are arthritis, cancer, aging, certain cardiovascular diseases. Many of the degenerative diseases in the human body are partially due to the interference of the synthesis of essential prostaglandin (local hormones) as we age. It is viewed that this is specifically due to the inhibition of the enzyme known as Delta-6-Desaturase. This enzyme normally converts essential unsaturated fatty acids in healthy cells to prostaglandin. Thus in the above list as well as in other degenerative conditions the enzyme is lacking or decreased and the effect is a decrease or lack of prostaglandin and therefore a disease condition in process.

An example of a well known antioxidant which protects blood cells as well as unsaturated fatty acids, which are a source of prostaglandin production is Vitamin E. Vitamin E also protects Vitamin A, another suspected source of prostaglandin production. Therefore, one of the purposes of this invention is the addition of one of the most powerful antioxidants, Pycnogenol (TM) from grape seed extract or the bark of the Merritime Pine tree. This antioxidant will protect both Vitamin A and E. It is common knowledge in the art that the production of free radicals (oxidants) do produce aging and disease. Also a genetic propensity is indicated in aging quickly or slowly as well as in most diseases such as cancer. It is also viewed that oxygen free radicals have a mutating effect upon cellular DNA/RNA. Thus the importance of the antioxidant is the invention under discussion.

In the detailed description of the invention to follow many of the ingredients are known powerful antioxidants which aid in free radical bonding and destruction and removal of same. Also the herbs as listed are descriptive in their particular functions based upon many thousands of years of traditional use in their respective arts. More recently said uses have been supported by scientific investigation.

In one embodiment, the invention is directed to a food supplement which comprises, in combination, (i) an extract which is stable for an indefinite amount of time in a dry state at ambient conditions, (ii) said extract being selected from, extracts prepared by aqueous or non-aqueous extractions of plant tissue, each said plant tissue being, respectively, selected from at least one member of a group consisting of roots, stems, seeds, rhizomes, flours, the entire plant tissue and mushrooms, (iii) in an orally ingestible carrier or diluent, (iv) each said plant tissue being, respectively, from a plant selected from the group consisting of *Arctium Lappa, Commiphoria Mukul, Curcuma longa, Echinacea Angustifolia, Echinacea Purpurea, Ganoderma Lucidium, Hydrastis Canadensis, Inula Helenium, Lens Esculenta, Lentinus Edodes,* papain, *Pisum Sativum,* Proanthocyanidins, *Terminalia Chebula, Trifolium Pratense, Ulmus Fulva, Verbascum Thapsus* and mixtures thereof, and optionally, further comprising, (v) extract of animal tissue selected from at least one member of the group consisting of adrenal gland bovine origin, lymphoid mass bovine origin, bovine pancreas, thymus gland bovine origin and mixtures thereof. The foregoing food supplement of at least one of the plant tissues comprises an antioxidant. Still further in the food supplement previously described, at least one of said plant tissues is a Proanthocyanidin.

In other embodiments of the invention, the food supplement described above further comprises at least one additional ingredient selected from the group consisting of (a) water soluble vitamins, (b) fat soluble vitamins, (c) unsaturated fatty acids, (d) their pharmaceutical acceptable salts, (e) and a carrier.

It is therefore the unique combinations of the enumerated components which give this remedy its' synergistic potency in the amelioration of degenerative diseases.

The plant tissues or extracts therefrom may be constituted by fresh or dehydrated roots, rhizomes, stems, leaves or fruits, depending upon the specific plant, mushroom or herb used.

DETAILED DESCRIPTION OF THE INVENTION

The present invention provides food supplements which are composed of plant extracted water soluble plant tissues and antioxidant compounds or individual ingredients. The plants, mushrooms or herbs are enumerated below. It should be noted that the antioxidant present in the compounds also will aid in preserving other substances within said compounds from deterioration. This is in addition to their inherent beneficial effects on human beings and/or the Mammalian Family in general.

After pulverizing of the plant materials by any mechanical method; extraction of the water soluble antioxidants and/or active chemical ingredients may be accomplished by use of a plant to water ratio of about 2:1 weight to volume. Extracted plant materials can be separated by any of the known methods in the art such as flotation, filtration, centrifugation and so on. In the discussion of this invention it is preferable to use the pulverized dried plants or mushrooms in their desiccated form. This also holds true for the antioxidant sources such as grape seed extracts or the bark of the Merritime Pine tree, re: Pycnogenol (TM).

The specific list of the components of this invention follow with a brief description of each of the ingredients or components in component form.

EXAMPLE 1

Food Supplement
1. Adrenal gland bovine origin. 150 mg. Cold pressed, source of DHEA (dehydroepiandrosterone), known for its antitumor effect. DHEA treatment inhibits tumor initiation as well as tumor promoter-induced epidermal hyperplasia and promotion of papillomas. There is much evidence that DHEA produces its antiproliferative and tumor preventive effects by inhibiting glucose-6-phosphate dehydrogenase and the pentose phosphate pathway. This pathway is an important source of NADPH, a critical reductant for many biochemical reactions that generate oxygen free radicals which may act as second messengers in stimulating hyperplasia.
2. *Arctium lappa* (burdock) 50 mg. Dried & ground roots & seeds. Contents: several volatile oils; inulin; tannin; and a bitter glycoside called artiin. Traditionally this herb is stated to act upon the respiratory, urinary, circulatory and lymphatic systems; contains an antimutagenic lignin-like compound.
3. *Commiphora Mukul; burseacea* (guggel) 250 mg. Resin of plant. Traditionally in ayurvedic medicine this resin acts on the nervous, circulatory, respiratory and digestive systems. It is specifically indicated and used for tumors, bronchitis, whooping cough, respiratory infections, and many other conditions. The chemistry is unavailable.
4. *Curcuma longa* (turmeric) 100 mg. Dried & ground rhizome traditionally this is a good natural antibiotic which also aids the digestion and the natural intestinal flora. Contains bitter principles, curcumin (a yellow pigment) and a volatile oil.
5. *Echinacea angustifolia* or *Echinacea purpurea* (cone flower) 200 mg. Dried & ground root & rhizome. Contents: it is viewed/stated that both angustifolia and purpurea have the identical chemistries but for the sake of stability I shall direct attention to *E. angustifolia*. There is a bacteriostatic principle termed echinacoside, a caffeic acid glycoside and a polysaccharide termed echinacin B, which forms a complex with hyaluronic acid that is resistant to attack by hyaluronidase. Also a hydrocarbon in the root oil termed (z)-1,8-pentadecadiene has definite in-vivo antitumor effects.
6. *Ganoderma lucidum* (mushroom) 100 mg. Dried & ground in its entirety. Traditionally known and used in oriental medicine for its antitumor effects. The chemistry is unavailable.
7. *Hydrastis canadensis* (golden seal) 50 mg. dried & ground rhizome. The chief compositions of this herb and mostly found in the rhizome are; the alkaloids berberine about 4% (C-20, H-17, NO4) which gives the yellow coloring to this chemical. Also hydrastine, about 4%; canadine; resin, lignin and a small amount of a volatile oil. Both berberine and hydrastine are noted for their astringent effect in inflammation of the mucous membranes; thus a calming effect is created in the lungs to quell cough and induce expectoration of mucous, at the same time soothing said membranes.
8. *Inula helenium* (elecampane or wild sunflower). 100 mg. Dried & ground rootstock & rhizome. The main chemical constituents are a chemical termed inulin also named alatin. This plant's root is in fact the richest source of inulin. The specific breakdown of constituents are; alanin (C-3, H-7, NO2); also termed amidopropionic acid; also alant-camphor (C-10, H-18, O); and an oily liquid termed helenin (C-15, H-20, O2). The traditional uses of the root are: diuretic, tonic, diaphoretic, expectorant, alterative, antiseptic, astringent and stimulant. The bitter active principle named helenin by Korab in 1885 showed that it was a powerful bactericide in general but specifically used on the tubercle bacillus.
9. *Lens esculenta* (lentil bean). 100 mg. Dried & ground bean. Wolf, quoted in "The Death of Cancer," Dr. Harold W. Manner, 1979 discovered a proteolytic-lipolytic enzyme within this bean which specifically destroys the protein coat of tumors. The specific chemistry is unavailable. When cancer cells proliferate, the DNA changes to single-stranded DNA. The *Lens esculenta* nucleases digest the single-stranded DNA. Also noted is the fact that proteases may facilitate metastasis of cancer cells; *Lens esculenta* protease inhibitors may prevent cancer metastasis, the same holds true for mung beans which may be used.
10. *Lentinus edodes* (shiitake mushrooms). 100 mg. Dried & ground in its entirety. Traditionally known for its antitumor effect in oriental medicine. The chemistry is unavailable.
11. Lymphoid masses bovine origin, from peyer's patches of intestinal tract. 200 mg. Freeze dried glands, ground. This has specific actions with increasing the immune system function and T-4 helper cells as in helping aids patients and in all auto-immune diseases.
12. Pancreas, bovine. 50 mg. Freeze dried gland ground. Noted for its' aid in breaking down the protein coats of tumors and the dissolving of mucous.
13. Papain (papaya enzyme). 50 mg. Extracted from dried fruit and leaves and then ground into powder. Noted for its specific action in breaking down the protein coats of tumors and the dissolving of mucous. Enzymatic chemistry is common knowledge.
14. *Pisum sativum* (garden pea). 50 mg. Dried whole crushed pea. Noted for its specific action in breaking down the protein coats of tumors and the dissolving of mucous.
15. Proanthocyanidins such as PYCNOGENOL (TM) from merritime pine tree bark or grape seed extract ground & dried. 300 mg. Noted as a strong antioxidant and free radical scavenger aiding in immunity.
16. *Terminalia chebula* (haritaki) 200 mg. Dried & ground fruit. Traditionally used in ayurvedic medicine on the digestive, excretory, nervous and respiratory systems. Amongst its many uses are indicated uses in cough, asthma, parasitic infections, tumors, jaundice, heart diseases and many other conditions. The chemistry is unavailable.
17. Thymus gland, bovine origin. 150 mg. Dried & ground/ cold pressed. This glandular extract has specific actions regarding the immune system and enhancing it as well as increasing the T4 helper cells as in helping aids patients and all auto immune diseases.

18. *Trifolium pratense* (red clover). 50 mg. Blossoms, dried & ground. Traditionally used in ayurvedic medicine on the circulatory, respiratory and lymphatic systems. It is indicated for coughs, bronchitis, infections and cancer. Its use as an anti-cancer agent is increased when used in conjunction with other herbs. Prolonged use may cause leukopenia.

19. *Ulmus fulva* (slippery elm). 500 mg. The inner bark dried & ground. A well known natural remedy for lung conditions used for centuries. It is an emollient, expectorant, diuretic and nutritive. It aids in healing lung hemorrhages and in the restoration of mucous membranes particularly of the lungs and stomach. The constituents are primarily a mucilage containing starch rich in calcium oxalate.

20. *Verbascum thapsus* (great mullein). 200 mg. Leaves & flowers dried & ground. This well known herb is used for its applications as a demulcent, emollient, antiseptic, astringent, pectoral, hemostatic, antispasmodic and anti-asthmatic amongst other uses. It is therefore specific for the lungs and other organs relative to healing mucous membranes. The leaves contain a mucilaginous bitter substance. This gum contains one to two percent of resin, a soluble bitter substance, an amoroid, tannin, saponin. The flowers contain a gum, resin, a yellow coloring principle, a green fatty substance resembling chlorophyll, a glucoside fatty matter, free phosphoric acid, uncrystalizable sugar, mineral salts mostly composed of potassium and calcium phosphates, a mucilaginous saponitic substance, a volatile oil and an astringent and sedative principles which are unidentified.

The foregoing components can be administered by oral administration, in unit dosage form, such as capsules (hard or soft), tablets or in the form of an elixir or tea. The food supplement according to the invention can take the form of a dispersion, suspension, capsule, tablet, pill, solution, powder, tea, syrup concentrate, spray or injectionable delivery system. Suitable pharmaceutical acceptable carriers, diluents and/or excipients maybe included to assist in tabletting, dissolution properties, etc. In the human adult, typical administration is one to three times daily as follows:

EXAMPLE 2

A composition comprising the following components
(a) adrenal gland bovine origin,
(b) Burdock,
(c) Guggel,
(d) Turmeric,
(e) Echinacea,
(f) Mushroom,
(g) Golden seal,
(h) Wild sunflower,
(i) Lentil or mung bean,
(o) lymphoid masses, bovine origin,
(k) Bovine pancreas,
(l) Papaya enzyme,
(m) Garden pea,
(n) Proanthocyanidins,
(o) Harataki,
(p) Thymus gland, bovine origin,
(q) Red clover,
(r) Slippery elm, and
(s) great mullein.

Total milligrams per capsule, tablets, or liquids is 2950. Dose at: two to three capsules, tablets, dried tea or liquid (two teaspoons) or any other delivery system three times per day, or as directed by your health care provider. To check for allergic reactions prior to use, open the contents of the capsule onto a drop or two of water which is placed on the wrist. Then place capsule contents onto the water, rub in and wait for five minutes. Remove the above. If a red rash appears this indicates a possible allergy to one of the above products. If this occurs do not use this product.

This product is not to be used during pregnancy, breast feeding or self administered. If taking other medication consult with your health care provider. If a blood cell problem occurs such as a decrease in white blood cells discontinue use and seek a physicians' advise.

Optionally 100 mg. of cold pressed lung tissue of bovine origin may be added for a direct effect to aid healing lung tissue.

It should be apparent that embodiments other than those specifically disclosed above come within the spirit and scope of the present invention. Hence, the present invention is not limited by the above description, but, rather, by the claims appended hereto.

What is claimed:

1. A food supplement which consists of, in combination
   (i) an orally ingestable carrier or diluent, and
   (ii) an extract which consists of a mixture of aqueous or non-aqueous extractions of plant tissue of each of the following plants:
   (a) *Arctium Lappa,*
   (b) *Commiphoria molmol,*
   (c) *Curcuma longa,*
   (d) *Ganoderma Lucidium,*
   (e) *Lens Esculenta,*
   (f) *Lentinus Edodes,*
   (g) *Pisum Sativum,*
   (h) *Terminalia Chebula,*
   (i) *Trifolium Pratense,*
   (j) *Verbascum Thapsus,* and at least one of
   (k) *Echinacea Angustifolia,* or
   (l) *Echinacea Purpurea.*

2. The food supplement of claim 1, wherein at least one said plant tissue comprises antioxidant.

3. The food supplement according to claim 1, further comprising at least one additional ingredient selected from the group consisting of (a) water soluble vitamins, (b) fat soluble vitamins, (c) unsaturated fatty acids, (d) their pharmaceutical acceptable salts (e) and a carrier.

4. The food supplement according to claim 1, in the form of a dispersion, suspension, capsule, tablet, pill, solution, powder, tea, or syrup concentrate.

5. The food supplement according to claim 2, which is in the form of a dispersion, suspension, capsule, tablet, pill, solution, powder, tea, or syrup concentrate.

6. A food supplement which comprises, in combination
   (i) an orally ingestable carrier or diluent, and
   (ii) an extract which consists of a mixture of aqueous or non-aqueous extractions of plant tissue of each of the following plants:
   (a) *Arctium Lappa,*
   (b) *Commiphoria molmol,*
   (c) *Curcuma longa,*
   (d) *Ganoderma Lucidium,*
   (e) *Lens Esculenta,*
   (f) *Lentinus Edodes,*
   (g) *Pisum Sativum,*

(h) *Terminalia Chebula,*
(i) *Trifolium Pratense,*
(j) *Verbascum Thapsus,* and at least one of
(k) *Echinacea Angustifolia,* or
(l) *Echinacea Purpurea;* and,
(iii) an extract of animal tissue selected from at least one member of the group consisting of adrenal gland bovine origin, lymphoid mass bovine origin, bovine pancreas and thymus gland bovine origin.

7. A food supplement which comprises, in combination
(i) an orally ingestable carrier or diluent, and
(ii) an extract which consists of a mixture of aqueous or non-aqueous extractions of plant tissue of each of the following plants:
(a) *Arctium Lappa,*
(b) *Commiphoria molmol,*
(c) *Curcuma longa,*
(d) *Ganoderma Lucidium,*
(e) *Lens Esculenta,*
(f) *Lentinus Edodes,*
(g) *Pisum Sativum,*
(h) *Terminalia Chebula,*
(i) *Trifolium Pratense,*
(j) *Verbascum Thapsus,*
(k) *Hydrastis Canadensis,*
(l) *Inula Helenium,*
(m) *papain*
(n) Proanthocyanidius,
(o) *Ulmus Fulva and* at least one of
(p) *Echinacea Angustifolia,* or
(q) *Echinacea Purpurea.*

8. A food supplement which composes, in combination
(i) an orally ingestable carrier, and
(ii) an extract which consists of a mixture of aqueous or non-aqueous extractions of plant tissue of each of the following plants:
(a) Mushroom;
(b) *Commiphoria molmol;*
(c) *Lens esculenta;*
(d) *Verbascum thaspsus.*

9. The food supplement of claim 8, further comprising, in combination
(iii) an extract of animal tissue selected from at least one member of the group consisting of adrenal gland bovine origin, lymphoid mass bovine origin, bovine pancreas and thymus gland bovine origin.

10. The food supplement of claim 8, further comprising at least one member selected from the group consisting of *Hydrasitis conadensis; Inula helenium, papin, Terminalia chebula* and *Ulmus fulva.*

11. The food supplement of claim 10, further comprising, in combination
(iii) an extract of animal tissue selected from at least one member of the group consisting of adrenal gland bovine origin, lymphoid mass bovine origin, bovine pancreas and thymus gland bovine origin.

12. The food supplement of claim 8, wherein said mushroom is *Lentinus edodes.*

\* \* \* \* \*

UNITED STATES PATENT AND TRADEMARK OFFICE
CERTIFICATE OF CORRECTION

PATENT NO.     : 6,440,448 B1 Page 1 of 1
DATED          : August 27, 2002
INVENTOR(S)    : Intelisano, Joseph It is certified that error appears in the above-identified patent and that said Letters Patent is hereby corrected as shown below:

<u>Column 2,</u>
Line 9, please replace "antioxidant" with -- antioxidant(s) --.
Line 26, please replace "flours" with -- flowers --.
Line 32, please replace "Mukul" with -- Momol --.

<u>Column 3,</u>
Line 40, please replace "Mukul" with -- Momol --.

Signed and Sealed this

Eleventh Day of March, 2003

JAMES E. ROGAN
*Director of the United States Patent and Trademark Office*